(12) United States Patent
Stefanov

(10) Patent No.: US 10,426,892 B2
(45) Date of Patent: Oct. 1, 2019

(54) MOTORIZED DRUG DELIVERY DEVICE

(71) Applicant: Carebay Europe Ltd., Sliema (MT)

(72) Inventor: Slobodan Stefanov, Deerfield Beach, FL (US)

(73) Assignee: SHL Medical AG, Zug (CH)

( * ) Notice: Subject to any disclaimer, the term of this patent is extended or adjusted under 35 U.S.C. 154(b) by 48 days.

(21) Appl. No.: 15/548,746

(22) PCT Filed: Mar. 8, 2016

(86) PCT No.: PCT/EP2016/054904
§ 371 (c)(1),
(2) Date: Aug. 3, 2017

(87) PCT Pub. No.: WO2016/146434
PCT Pub. Date: Sep. 22, 2016

(65) Prior Publication Data
US 2018/0036482 A1 Feb. 8, 2018

(30) Foreign Application Priority Data
Mar. 13, 2015 (EP) ...................................... 15158985

(51) Int. Cl.
*A61M 5/24* (2006.01)
*A61M 5/315* (2006.01)

(52) U.S. Cl.
CPC ............. *A61M 5/24* (2013.01); *A61M 5/3156* (2013.01); *A61M 5/31545* (2013.01);
(Continued)

(58) Field of Classification Search
CPC .. A61M 5/24; A61M 5/2422; A61M 5/31545; A61M 5/3156;
(Continued)

(56) References Cited

U.S. PATENT DOCUMENTS

| | | | |
|---|---|---|---|
| 2007/0073228 A1* | 3/2007 | Mernoe | A61M 5/14244 604/131 |
| 2015/0126926 A1* | 5/2015 | Giambattista | A61M 5/1454 604/135 |
| 2018/0036482 A1* | 2/2018 | Stefanov | A61M 5/24 |

FOREIGN PATENT DOCUMENTS

| | | |
|---|---|---|
| WO | 2006105792 A1 | 10/2006 |
| WO | 2013153041 A2 | 10/2013 |

* cited by examiner

*Primary Examiner* — Bhisma Mehta
*Assistant Examiner* — Nidah M Hussain
(74) *Attorney, Agent, or Firm* — McDonnell Boehnen Hulbert & Berghoff LLP

(57) ABSTRACT

A motorized drug delivery device configured to administer at least one pre-set dose of a medicament contained within a medicament container. The delivery device comprising a user activation system (13), a motor (22), a gear train (15) operatively coupled to the user activation system and the motor, and a piston plunger system (200) operatively coupled to the gear train. The piston plunger system comprises a piston plunger (50) and at least one plunger extension (42; 44) for extending a length of the piston plunger. The piston plunger system is configured to act on a stopper contained within the medicament container to deliver at least one pre-set dose of medicament. The user activation system comprises a mechanical automatic reset activation system for automatically resetting the drug delivery device after administration of the pre-set dose.

19 Claims, 14 Drawing Sheets

(52) U.S. Cl.
CPC . *A61M 5/31593* (2013.01); *A61M 2005/3152* (2013.01); *A61M 2005/31518* (2013.01); *A61M 2005/31588* (2013.01); *A61M 2205/6027* (2013.01)

(58) Field of Classification Search
CPC ........... A61M 2005/2026; A61M 2005/31518; A61M 2005/31588; A61M 2005/3152
USPC ........................................................ 604/218
See application file for complete search history.

MOTORIZED DRUG DELIVERY DEVICE

CROSS REFERENCE TO RELATED APPLICATIONS

The present application is a U.S. National Phase Application pursuant to 35 U.S.C. § 371 of International Application No. PCT/EP2016/054904 filed Mar. 8, 2016, which claims priority to European Patent Application No. 15158985.0 filed Mar. 13, 2015. The entire disclosure contents of these applications are herewith incorporated by reference into the present application.

FIELD

The present disclosure relates to injection devices and methods of delivering a plurality of set or predetermined doses of a medicament to a user. Specifically, the present disclosure relates to injection devices comprising a mechanical automatic reset activation system that can be used to administer a plurality of pre-set or predetermined doses of a medicament contained within a medicament container. The injection device may comprise a semi-reusable device or a disposable device.

BACKGROUND

Injection devices are generally known for the self administration of a medicament by patients. As just one example, those patients suffering from diabetes may require repeated injections of insulin. Other patients may require regular injections of other types of medicaments, such as a growth hormone. Some injection devices allow the patient to select a dose of a medicament contained within the injection device and to administer this selected dose. Setting or selecting a specified dose may be a particular problem for the elderly, the infirm, those suffering from vision difficulties and those suffering from diabetes related problems which impair their faculties.

Injection devices typically contain a medicament that may be contained in a conventional medicament container that is located within the injection device. Such conventional medicament containers, e.g. cartridges, typically comprise a bung or stopper at one end of the medicament container (i.e., the proximal end). It is this bung or stopper that is typically driven towards a second end (i.e., a distal end) of the medicament container to expel the medicament from the injection device, preferably by way of an attached double ended needle assembly.

One problem that often arises with certain conventional injection devices used for self-administration is the actual size of the injection device. For example, it is a problem that injection devices should be small or compact enough to fit into a jacket pocket or a hand bag without much difficulty. At the same time, the injection device must be of a size that enables a piston rod or a piston rod system used to drive the medicament container bung within the medicament container so that the bung can be moved both to a maximum dispense position within the medicament container and, in the case where the injection device comprises a reusable injection device, to be fully withdrawn from the medicament container to allow for replacement of the spent medicament container with a new, full medicament container.

A number of factors may affect the design of injection devices. One such factor is the size of the device. The injection device may be sized to house the various drive components, yet a large device may reduce the portability for the user. Another factor that may affect the design of an injection device is the convenience to the user. For example, some injection devices are designed with a complicated or sophisticated user interface that requires a certain degree of learning as to how to set a dose, how to administer the set dose, and then how to reset the device after dose administration. Indeed, a number of injection device components can impact the overall size and portability of an injection device and therefore can impact convenience to the user.

There is, therefore, a general need for an injection device that can be quickly and easily used by a typical patient for self administration of such drugs, such as insulin or human growth hormones. In addition, there is a general need to an injection device that can be quickly and easily used to administer at least one and perhaps multiple preset or predetermined doses. There is, therefore, a general need for an injection device that can quickly and easily administer a plurality of preset doses. With such an injection device, there is also a need for a device that can quickly and efficiently reset itself so that the device stands ready for the next dose administration. There is, therefore, a need for a compact and portable drug delivery device that can administer one or more preset devices and that does not include an intricate and complicated user interface for dose setting, for dose administration, and preparing the injection device for the next dose setting and dose administration procedures.

These and other advantages will become evident from the following more detailed description of the invention.

SUMMARY

The present disclosure is directed to a multiple injection device that is motor operated. A motorized drug delivery device configured to administer at least one pre-set dose of a medicament contained within a medicament container. The delivery device comprising a user activation system, a motor, a gear train operatively coupled to the user activation system and the motor, and a piston plunger system operatively coupled to the gear train. The piston plunger system comprising a piston plunger and at least one plunger extension for extending a length of the piston plunger. The piston plunger system is configured to act on a stopper contained within the medicament container to deliver at least one pre-set dose of medicament.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawing, in which.

DETAILED DESCRIPTION

Figure 1:
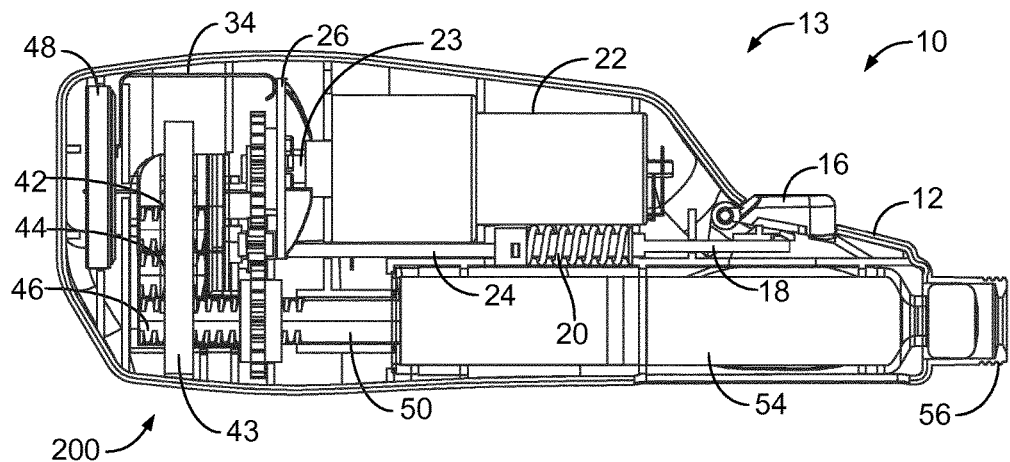
FIG. 1 illustrates a plan view of a motorized injection device in accordance with one aspect of the present disclosure, with one housing part removed for clarity.
Figure 2:
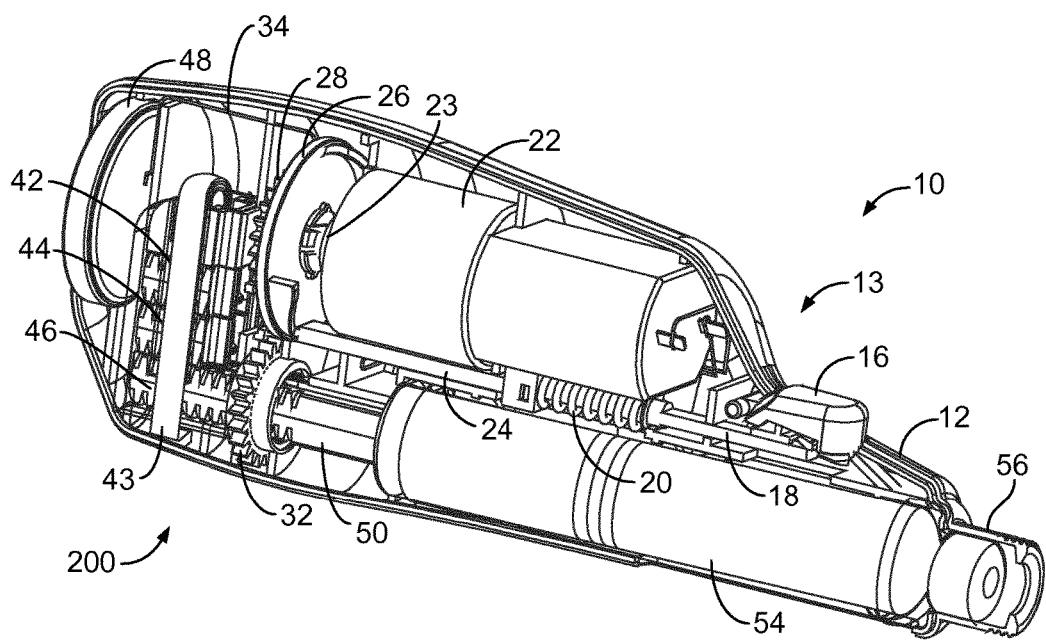
FIG. 2 illustrates a perspective view of the injection device illustrated in FIG. 1, with one housing part removed for clarity.

FIG. 1 illustrates a plan view of a motorized injection device in accordance with one aspect of the present disclosure, with one housing part removed for clarity. FIG. 2 illustrates a perspective view of the injection device illustrated in FIG. 1, with one housing part removed for clarity. And FIG. 3 illustrates an exploded view of the injection device 10 illustrated in FIGS. 1 and 2.

Figure 3:
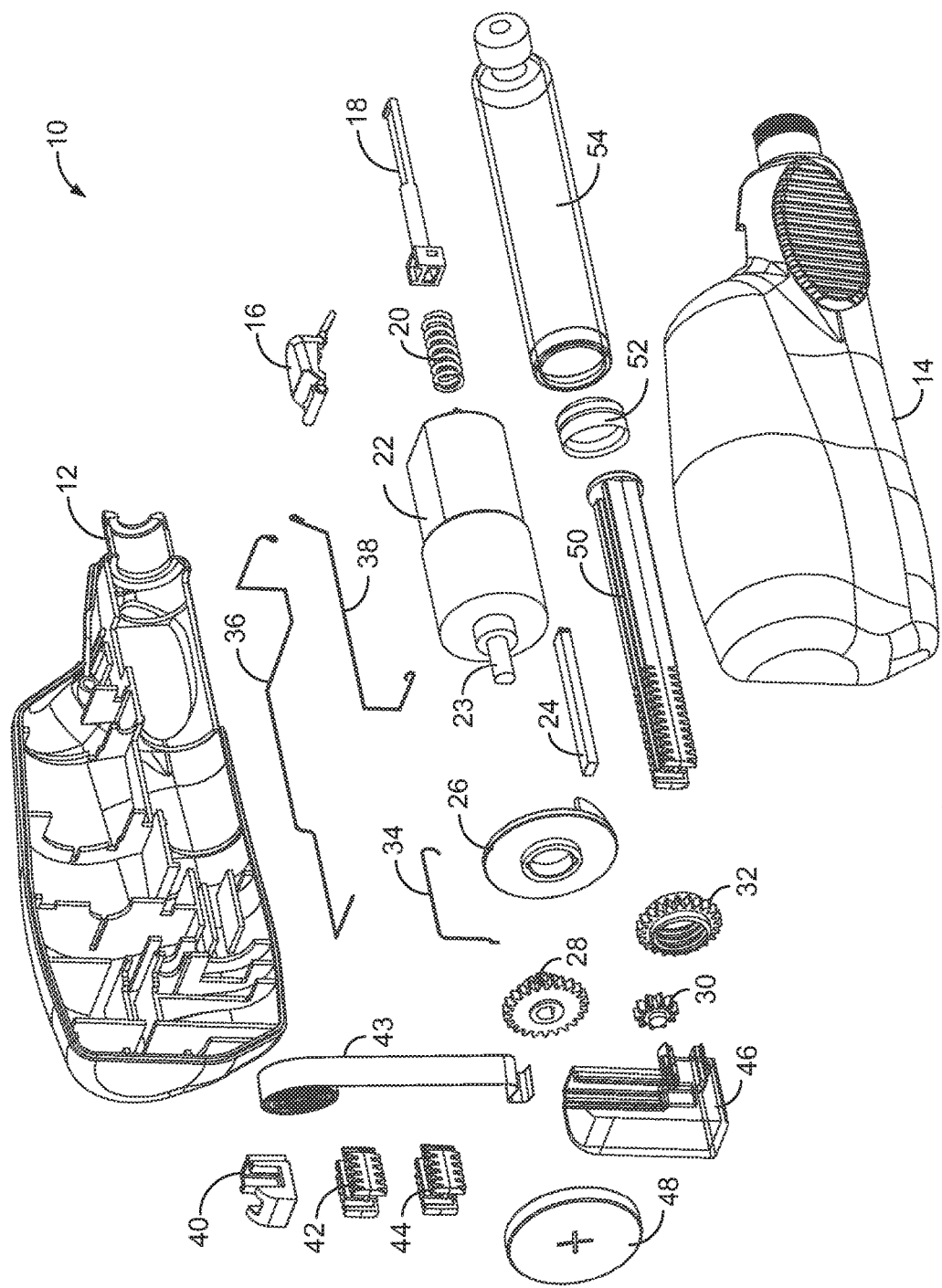
FIG. 3 illustrates an exploded view of the injection device illustrated in FIGS. 1 and 2.

Referring to FIGS. 1-3, the injection device 10 utilizes an electro-mechanical drive train to deliver at least one and preferably a plurality of pre-set doses of a single medicament contained within a medicament container 54 contained within the injection device 10. Preferably, the injection device is a disposable device wherein the medicament container 54 cannot be removed and replaced with a new, full medicament container. As such, with such a disposable injection device arrangement, once the medicament within the medicament container is depleted, the injection device is discarded.

In an alternative arrangement, the injection device 10 comprises a reusable injection device. With such a reusable injection device, once the medicament contained within the medicament container 54 is depleted, the medicament container 54 may removed and replaced with a new medicament container.

Preferably, the medicament container 54 comprises a conventional medicament container. As can be seen from FIGS. 1-3, such a conventional medicament container (often referred to in the relevant art as an ampoule) typically includes a reservoir that is filled with a medication (e.g., insulin) 100 and can contain 100 to 300 units of medication. In such a conventional medicament container, a movable rubber type bung or stopper 102 is located at one end (e.g., a proximal end) of the medicament container reservoir. In addition, a top having a pierceable rubber seal 104 located at the other, often necked-down, end (e.g., a distal end). A crimped annular metal band or ferrule 106 is typically used to hold the rubber seal in place. While the medicament container housing may be typically made of plastic, medicament container reservoirs have historically been made of glass.

A distal most end of the drug injection device comprises a needle or cannula connecting mechanism 56. In one preferred arrangement, the cannula connecting mechanism 56 of the drug delivery device 10 is configured for use with a double ended needle assembly. The needle assembly is typically a replaceable double-ended needle assembly. Before an injection, a replaceable double-ended needle assembly is attached to one end of the medicament container assembly, a dose is set, and then a dose is administered. Such removable needle assemblies may be threaded onto, or pushed (i.e., snapped) onto the distal end of the injection device 10 so that a proximally directed needle of the needle assembly pierces the pierceable seal located at the distal end of the medicament container 54.

As illustrated in FIGS. 1-3, the drug delivery device 10 comprises a injection device housing which comprises, in this illustrated embodiment, two component parts: a first housing part 12 and a second housing part 14.

Once a user activates the injection device 10, the injection device will administer a preset or predetermined amount of medicament from the medicament container 54. Conveniently, upon the administration of the preset dose and without further user intervention, an mechanical automatic reset activation system 13 of the injection device (as described in greater detail below) automatically resets itself so that the injection device 10 stands ready to be operated again so as to administer another pre-set dose of medicament from the medicament container 54. Therefore, one advantage of the presently disclosed injection device 10 is that the user is not called upon to manually reset the injection device after a dose administration procedure in order to prepare the injection device for the next dose administration procedure.

In one preferred arrangement, this automatically resettable user activation system 13 comprises a mechanical system comprising a dispense button 16, a hook release 18, a biasing member or a spring 20, and, a connection rod 24. As illustrated, the dispense button 16 resides near a distal end of the injection device 10 and available for user activation as it resides along a top surface of the first and second housing parts 12, 14. In one preferred arrangement, the dispense button 16 comprises a pivoting dispense button that, in a ready position (as illustrated in FIGS. 1 and 2), can be depressed. Once depressed and then released, the pivoting dispense button 16 returns to its ready position.

In addition, the drug delivery device 10 further includes a motor 22 that is operatively coupled to a gear train 15. As illustrated, the motor 22 is situated above of the auto reset activation system 13 and resides near the before the gear train 15. In such a preferred arrangement, an output shaft 23 of the motor 22 can be operably coupled to the gear train 15. In this illustrated arrangement, the gear train 15 comprises a gear disc 26, a driving gear 28, a transfer gear 30, and a driven gear 32. Specifically, the output shaft 23 of the motor 22 is operatively coupled to the gear disk 26 as will be explained in greater detail below.

The drug delivery device 10 further comprises a multi-segmented piston plunger system 200. As will be explained in greater detail below, this multi-segmented piston plunger system 200 comprises one or more plunger extensions. In one preferred arrangement, the piston plunger system 200 comprises a first plunger extension 42 and a second plunger extension 44. However, as those of ordinary skill in the relevant art will recognize, alternative piston plunger extension arrangements may also be utilized. As just one example, more than two plunger extensions may be desired, for example, to take into account an injection device comprising a larger medicament container than as illustrated in FIGS. 1 and 2.

The multi-segmented piston plunger system 200 is operatively coupled to the gear train 15. In this illustrated arrangement, the multi-segmented piston plunger system 200 comprises a magazine fixture 40, a plurality of plunger extensions (i.e., a first plunger extension 42 and a second plunger extension 44), a magazine body 46, a magazine flat band spring 43, a piston plunger 50, and a stopper 52. The stopper, however, is included in the medicament container 54 when assembled with the delivery device. The operation of the multi-segmented piston plunger system 200 will be described in greater detail with respect to FIGS. 14a and 14b along with FIGS. 15a and 15b.

The drug delivery device 10 further includes an injection circuit 250 (see FIG. 9) wherein this injection circuit is completed whenever a user activates the automatic reset activation system 13, preferably by activating the dispense button 16. In one preferred arrangement, this injection circuit 250 comprises a battery 48, and a plurality of circuit conductors 252 that are operatively configured to conduct current from the battery 28 to motor connectors 23 provided at the front of distal end of the motor 22, near the dispense button 16. In this illustrated arrangement, the circuit of conductors 252 comprises a battery-gear disc conductor 34, a battery-motor conductor 36, and a connection rod-motor conductor 38.

Figure 4A:
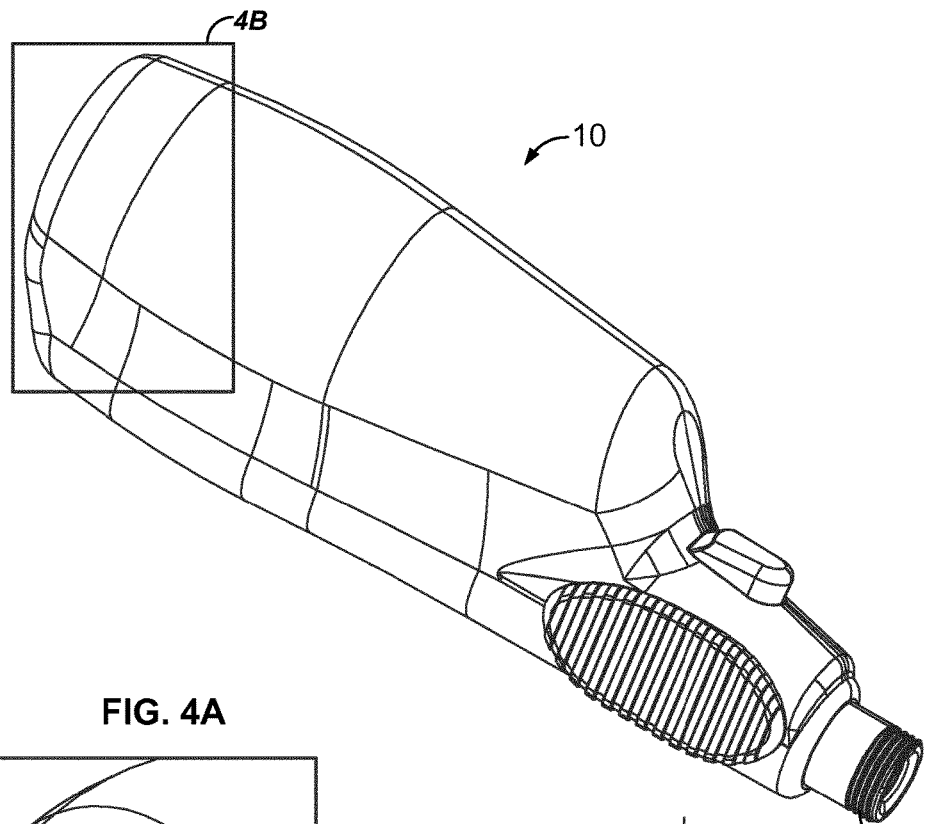
FIG. 4A illustrates a perspective view of the injection device illustrated in FIG. 1, with both the first housing part and the second housing parts attached.
Figure 4B:
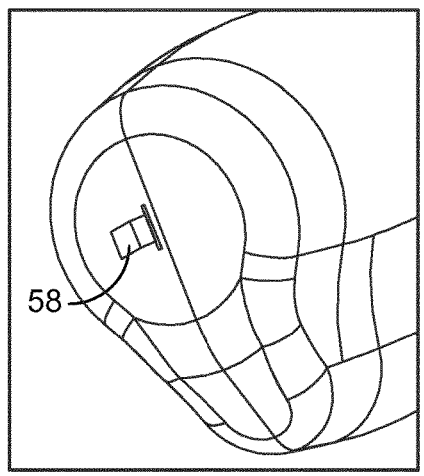
FIG. 4B illustrates a cut-out view of a proximal end of the injection device.
Figure 4C:
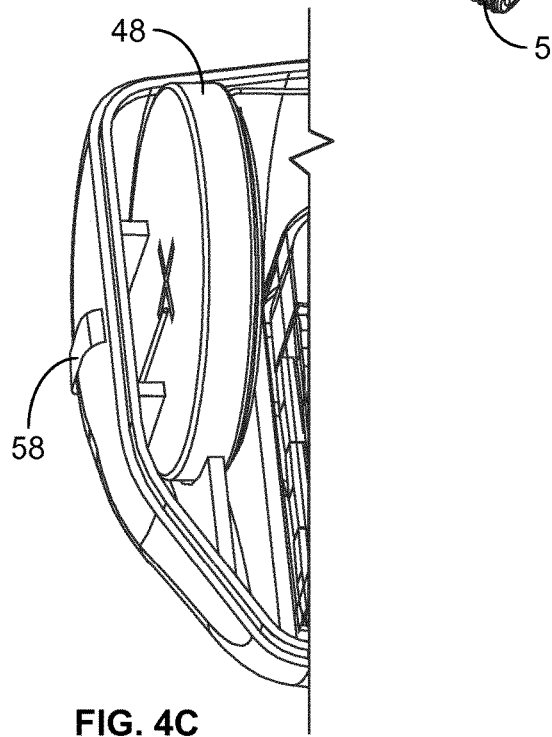
FIG. 4C illustrates a detailed cut-away view of the proximal end of the injection device illustrated in FIG. 1, with the top housing part removed for clarity.

In one preferred arrangement, the drug delivery device 10 may be stored and shipped with a user activated tab 58. For example, FIG. 4a illustrates a perspective view of the injection device 10 illustrated in FIG. 1, with both the first housing part and the second housing parts attached and a cut-out view of a proximal end of the injection device illustrating a user activated tab 58. Similarly, FIG. 4b illustrates a detailed cut-away view of the proximal end of the injection device illustrated in FIG. 1, with the top housing part removed for clarity.

Such a user activated tab 58 allows the drug delivery device to transition from a locked or un-usable state to an unlocked or usable state. As just one example, such a user activated tab 58 may be used when the injection device 10 is shipped from the manufacturer to the user so as to prevent undesired activation of the injection device 10. It can also prevent the undesired draining of the drug delivery device power source, such as a battery 48 prior to use. As such, in order to begin activation of the injection device 10, this user activated tab 58 must be user pulled out of or removed from the injection device 10 in order to activate the injection device 10 so as to allow dose administration.

FIG. 4a illustrates a perspective view of the device illustrated in FIG. 1. As illustrated, both housings attached and a cut-out view of the proximal end of the injection device. FIG. 4b illustrates a detailed top view of the proximal end of the device illustrated in FIG. 1, with the top housing part removed for clarity. Referring to FIGS. 4a and 4b, in one arrangement, the drug delivery device 10 comprises a user activated tab 58 near the proximal end of the device. In this illustrated arrangement, the injection device battery 48 is located adjacent a back wall of this housing and therefore contained in the proximal end section of the housing, near the user activated tab 58. In one preferred arrangement, the tab 58 may be made of plastic. As such, a user must first pull out or remove the tab in order to activate the device. In one arrangement, the tab resides between a first surface of the battery 58 and one end of the battery-motor conductor 36. Therefore, in order to activate the drug delivery device 10 and allow the battery-motor conductor 36 to make with the first surface of the battery, a user must pull on the tab so as to then remove tab 58 in order to connect the battery-motor wire 36 with the battery 48. FIG. 4b illustrates a close up sectional view illustrating the tab and battery connection. One advantage of utilizing such an activating tab 58 is the unintended activation of the drug delivery device, such as during transportation or non-use of the device.

When a user is ready to use the drug delivery device 10, the user attaches a needle assembly to the distal end of the drug delivery device 10. Such a needle assembly may comprise a conventional double ended needle (see, e.g., double ended needle assembly 100 FIG. 16), typically used with pen type injection devices. In this illustrated arrangement, the distal end of the drug delivery device comprises a connecting mechanism 56 by way of a thread. Such a thread may comprise a single or double start thread. The needle may therefore be threaded or screwed onto this thread portion 56. Alternative connection mechanisms may also be used. For example, an axial connection mechanism may also be used wherein the needle is attached by merely axially placing the needle onto the distal end of the drug delivery device. Such known axial attachment means include snap locks, snap fits, snap rings, keyed slots, and combinations of such connections.

The drug delivery device 10 is then primed by activating it one or more times. Priming of the delivery device 10 may take place by pointing the injection device and the distal or needle end of the device upwards, and pressing the pivoting member until a first few drops of the medicament appear at the tip of the attached needle assembly. Priming is ordinarily recommended in order to eliminate the air from the medicament container and injection system.

As noted above, the drug delivery device 10 comprises a user activation system 13 that allows the user to activate the injection device for delivery. In this illustrated arrangement, the user activation system 13 comprises a dispense button 16, a hook release 18, a biasing member or a spring 20, and a connection rod 24. Dose administration of the predetermined dose is initiated when a user activates the device by pressing the dispense button 16. Once the drug device 10 has been primed, it is now available to deliver a plurality of set or fixed doses from the medicament container 54. As just one example, the drug delivery device 10 may be designed to deliver approximately twenty (20) preset doses from the medicament container. As those of ordinary skill in the relevant art will recognize, alternative preset dosing arrangements may also be used.

Figure 5A:
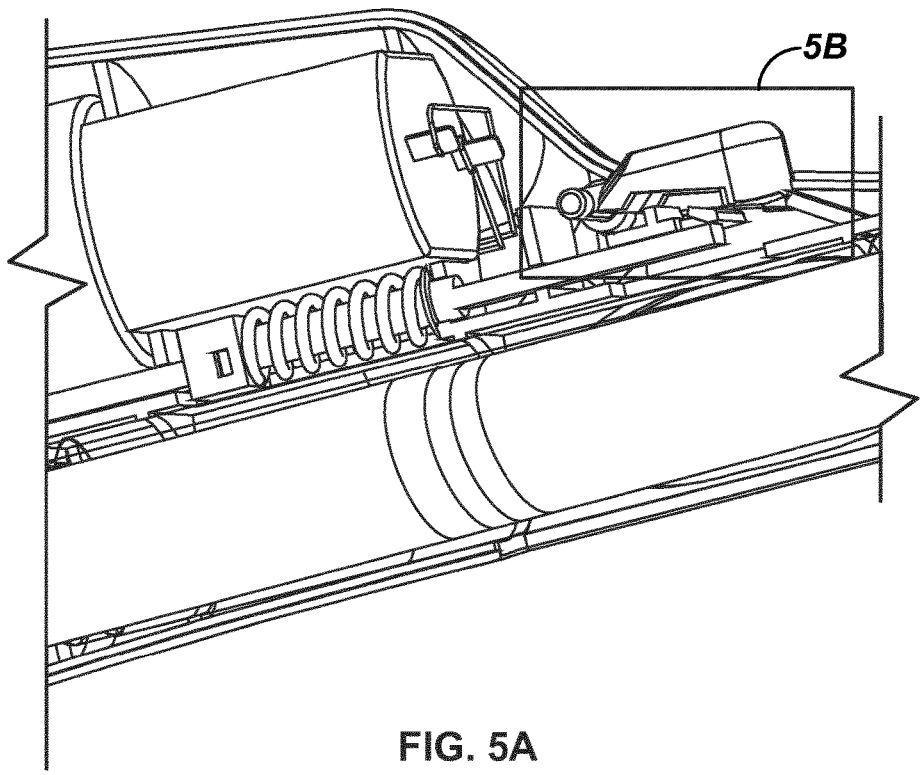
FIG. 5A, B illustrate detailed views of the mechanical automatic reset user activation system of the injection device illustrated FIG. 1.
Figure 5B:
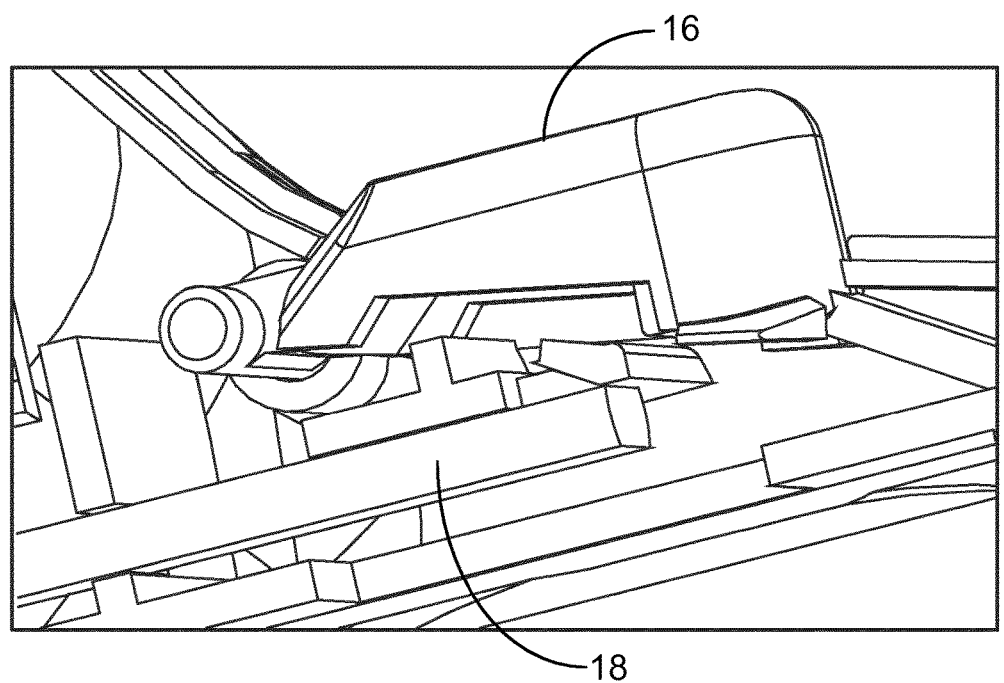

The dispense button 16 is also used as the dose button. For example, FIG. 5 illustrates a detailed view of the mechanical auto reset user activation system 13 of the injection device illustrated FIG. 1, including the dispense button 16 and the dose buttons' interaction with the hook release 18. Also illustrated in FIG. 5, prior to activation, the interaction of the connecting rod with the hook release 18 and that the spring or biasing element initially resides in a compressed state. As illustrated in FIG. 5, a distal end of the hook release 18 is operatively coupled to a bottom portion of the dispense button 16. In addition, and as illustrated, a distal end of the connection rod 24 is operatively connected to a proximal end of the hook release 18. The biasing member or spring 20 surrounds at least a proximal end portion of the hook release 18. The spring 20 acts upon this hook release so as to urge the hook release 18 in the proximal direction but is (as illustrated) constrained by the connected nature of the dispense button and the hook release 18. This spring 20 resides in a compacted or a compressed state and as illustrated is maintained in this compacted or compressed state by way of a ledge located at a distal end of the motor 22 and a proximally located block portion of the hook release 18 (directly adjacent a distal front end of the connecting rod 24).

Before activation of the dose button 16, a proximal end of the dispense button 16 is pivotally mounted between the first housing part 12 and the second housing part 14. In this illustrated arrangement, when a distal portion of the dispense button 16 is pressed inwardly (downward) in the direction of arrow A, the dispense button 14 engages with the hook release 18 in order to remove the contact between the hook release 18 and the first and second housing parts 12 and 14. As the hook release 18 is released from the dispense button, this allows the compacted spring 20 to contract or expand. Expanding the spring 20 thereby urges the hook release 18 (along with the connected connection rod 24) in the proximal direction, towards the gear train 15.

Figure 6:
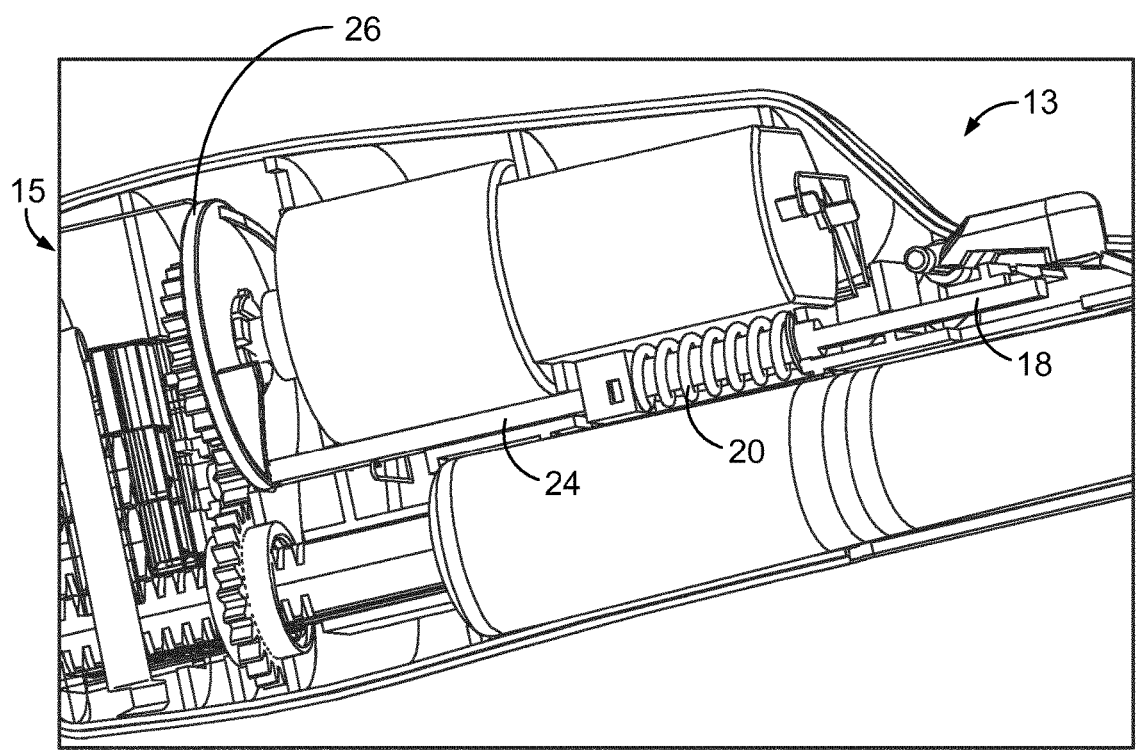
FIG. 6 illustrates a detailed view of the mechanical automatic reset user activation system and a portion of the gearing system of the injection device illustrated FIG. 1.

The hook release 18 is operatively coupled to a connection rod 24 and moves along with the connection rod both in the distal and proximal direction. As such, under the urging of the spring 20, both the hook release 18 and the connection rod 24 move proximally in an axial direction toward the proximal end of the drug delivery device 10 as the spring 20 extends. FIG. 6 illustrates a detailed view of the mechanical auto reset user activation system 13 and a portion of the gearing system of the injection device illustrated FIG. 1, including a detailed view of the "unreleased" hook release 18 and connection rod 24 of FIG. 1 being driven proximally under the urging of the spring 20. The connection rod 24 is moved in the proximal direction until its most proximal end makes contact with a component of the gear train 15.

As noted above, the drug delivery device 10 further comprises a gear train 15 and in this illustrated arrangement, the gear train 15 comprises a gear disc 26, a driving gear 28, a transfer gear 30, and a driven gear 32. As noted above, an output shaft of the motor 22 is operatively coupled to the gear disk 26 such that, once the motor is energized, the gear disc 26 will rotate at the same speed as the output shaft of the motor.

Figure 7A:
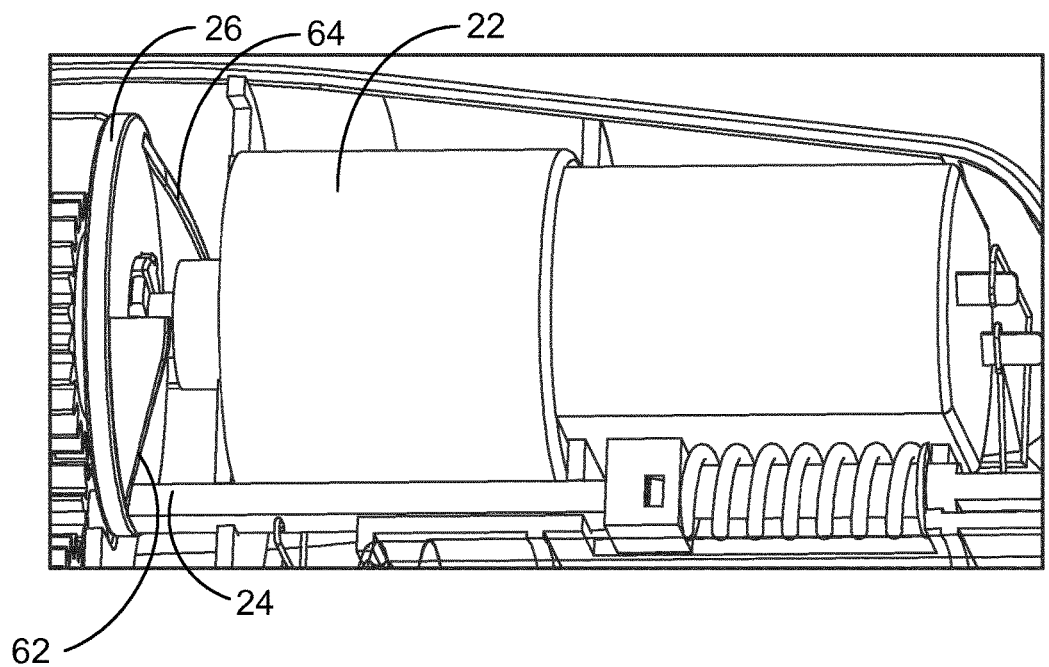
FIG. 7A illustrates a detailed view of the connection rod and the gear disk of FIG. 1, with the connection rod in contact with the gear disk.

FIG. 7a illustrates a detailed view of the connection rod and the gear disk of FIG. 1, with the connection rod in contact with the gear disk. In this illustrated arrangement, the gear disc 26 and the connection rod 24 are both made of a conducting material (such as copper or the like). Contact between a proximal end of the connection rod and the distal surface of the gear disc 26 completes the circuit for the motor 22, thereby providing power from the battery to 48 to the motor by way of the circuit, thereby allowing the injection process to begin.

Figure 8A:
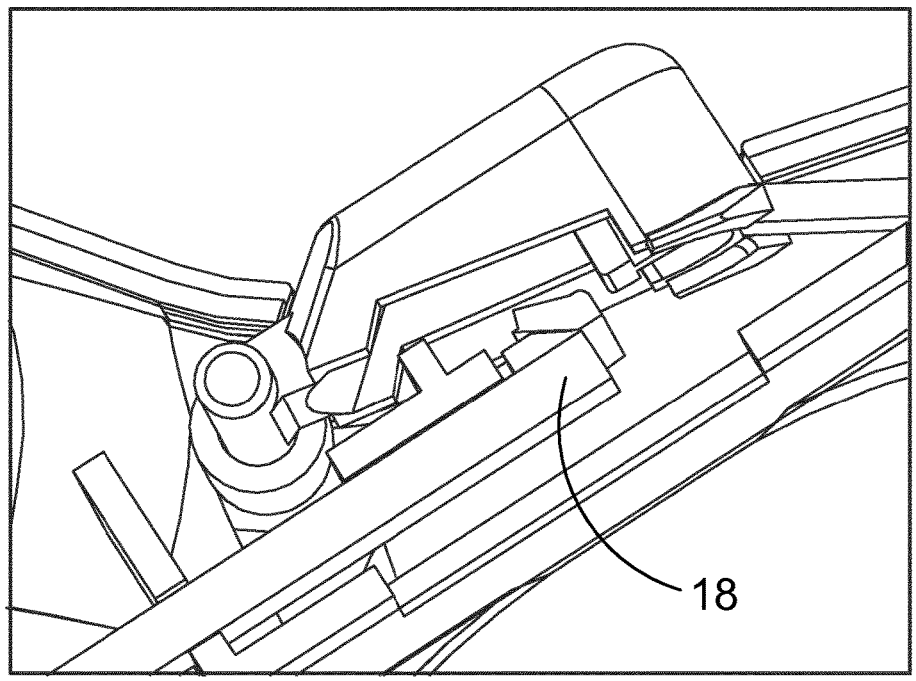
FIG. 8A illustrates a detailed view of the hook release in the second position.

When the connection rod 24 contacts the gear disc 26, the hook release 18 is in a second position as illustrated in FIG. 8a. The gear disc 26 is operatively coupled to a drive shaft of the motor, such that, when the motor is activated, the output shaft of the motor 22 will rotate the gear disc 26 in a desired direction and at a desired speed.

Figure 7B:
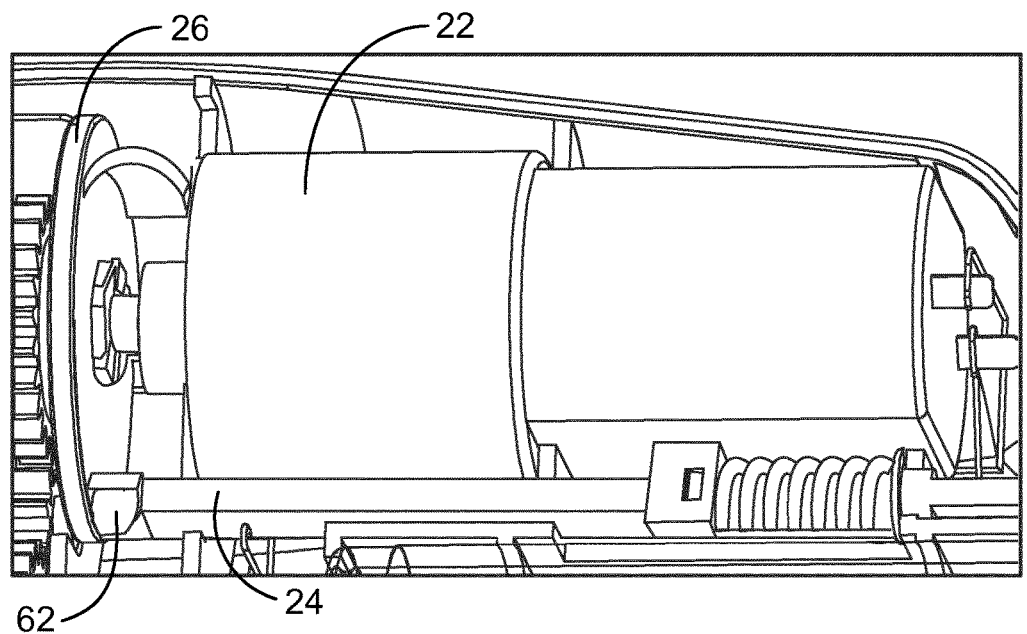
FIG. 7B illustrates a detailed view of the inclined walls rising the connection rod as the motor rotates.

In addition, the first surface of the gear disc 26 comprises a first inclined wall 62 and a second inclined wall 64. In this illustrated arrangement, there are two walls 62, 64 so as to achieve a specific desired dose from the medicament container 54, e.g., 30 Units of medicament. Depending of the size of the desired or targeted dose, a greater or lesser number of ramps may be utilized. The first and second inclined walls 62 and 64 are configured such that, when the motor is operated to turn its output shaft and hence the gear disc 26, as the connection rod resides adjacent the first surface of the gear disc, the gear disc rotation will cause the first and second inclined surface to engage the proximal end of the connection rod. And when the proximal end of the connection rod engages either the first or the second inclined walls, the connection rod 24 will ride up the inclined wall and therefor drive the connection rod 24 back in the distal direction towards the dispense button as illustrated in the direction of the arrow shown in FIG. 7b as the motor 22 spins.

Figure 8B:
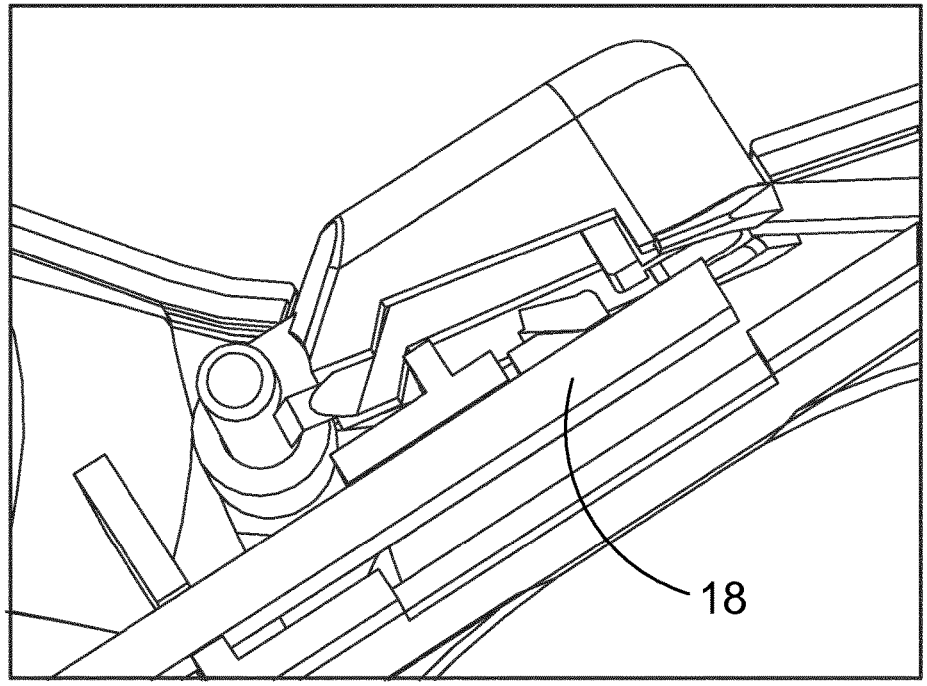
FIG. 8B illustrates a detailed view of the hook release in the first position.

As the connection rod 24 and hence the hook release are driven back in the distal direction towards the dispense button 16, this causes the hook release 18 to reset and therefor return to its original engaged position, as illustrated in FIGS. 1 and 2. As the gear disc 26 continues to rotate, the hook release 18 makes contact with the first and second housing parts 12 and 14, locking it in its first position (shown in FIG. 8b). The gear disc 26 continues to rotate and the connection rod 24 reaches the end of the inclined wall 62. This removes the connection between the gear disc 26 and the connection rod 24, which is locked up, thus disconnecting the circuit. See FIGS. 7a, 7b, 8a, and 8b. Pushing the connecting rod in the distal direction back to its original position will also recharge the spring 20.

Figure 9:
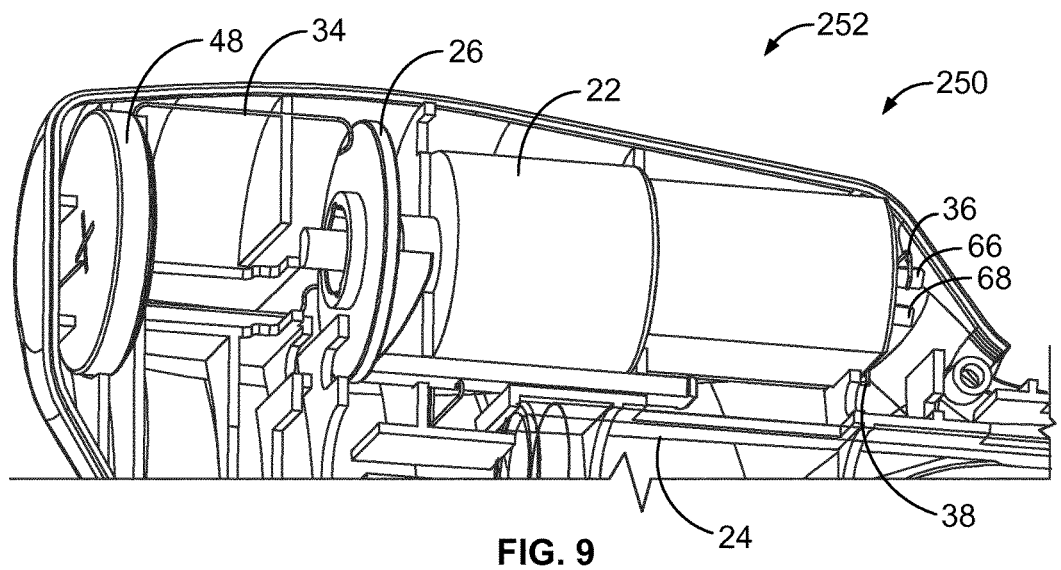
FIG. 9 illustrates a detailed view of an injection circuit configuration for use with the injection device illustrated in FIGS. 1 and 2.

As noted above, the drug delivery device further comprises an injection circuit 250. For example, FIG. 9 illustrates the injection circuit 250 which in this illustrated embodiment is defined by a plurality of conductors 252. For example, in one arrangement, the injection circuit 250 may be defined by the following conductors 252: a battery-gear disc conductor 34, a battery-motor conductor 36, and a connection rod-motor conductor 38. The battery-gear disc conductor 34 is connected to a front surface of the battery 48 and positioned to be in constant contact with a rear surface of the rotating gear disc 26. The battery-motor conductor 36 is connected to a rear or proximal surface of the battery 48 and a first connector 66 located at the distal end on the motor 22. The last connection is made with the connection rod-motor conductor 38, which is in constant contact with the connection rod 24 and is connected to a second connector 68 of the motor 22. As such, when the connection rod 24 contacts the gear disc 26, the battery-gear disc conductor 34 and the connection rod-motor conductor 38 define a single conduction path thereby completing the injection circuit. Once such an injection circuit 250 has been completed, initiation the injection of the set dose may take place.

Figure 10:
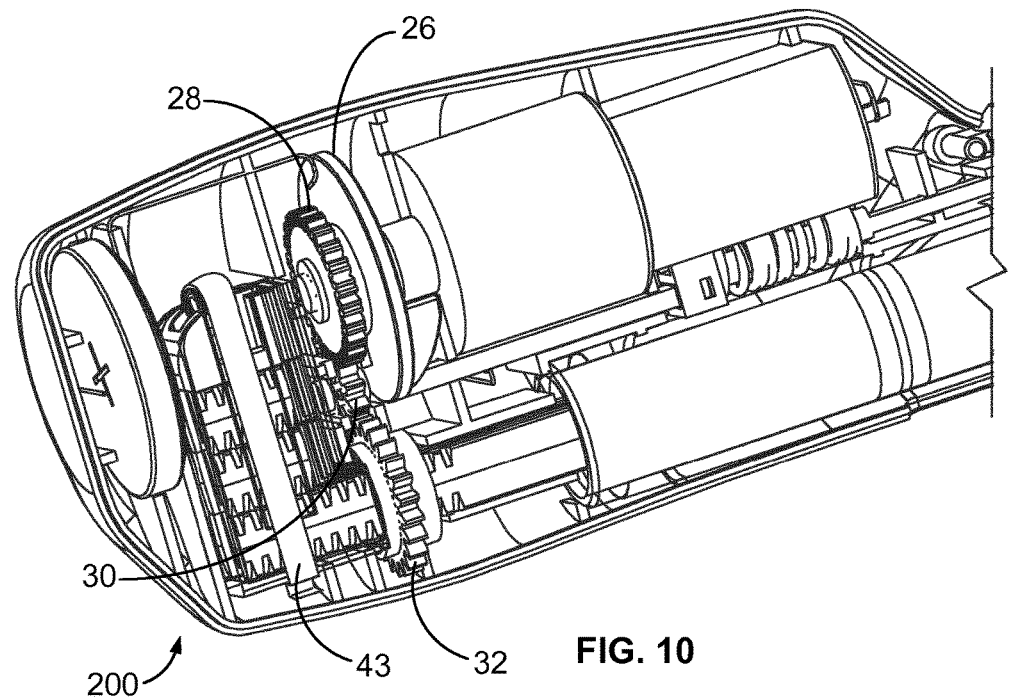
FIG. 10 illustrates a detailed view of the gear assembly.

In addition, the drug delivery device 10 further includes a motor 22 that is operatively coupled to a gear train 15. FIG. 10 illustrates a detailed view of the gear train 15 and its various component parts. Specifically, in this illustrated arrangement, the gear train comprises a gear disc 26, a driving gear 28, a transfer gear 30, and a driven gear 32. As shown in FIG. 10, the gearing in the system (driving gear 28, transfer gear 30, driven gear 32) rotates along with the gear disc 26. This is what is responsible for delivering the dosage of medicament. The dosage is delivered by a gear train 15 comprising the driving gear 28, the transfer gear 30, and the driven gear 32.

Figure 11A:
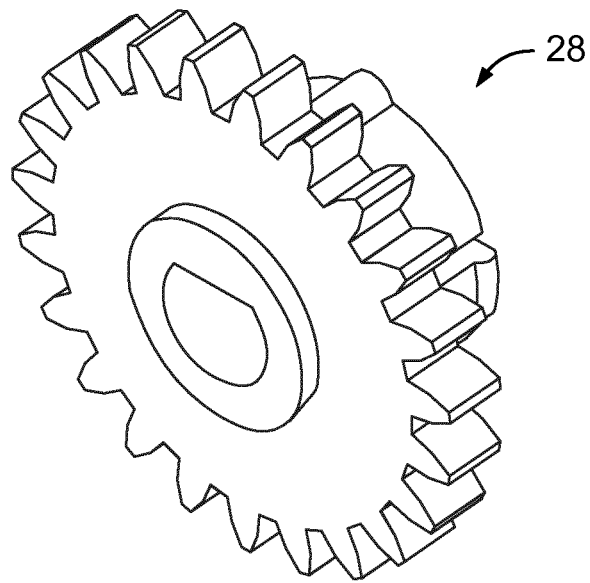
FIG. 11A illustrates a distal perspective view of the driving gear for use with the gear assembly illustrated in FIG. 10.
Figure 11B:
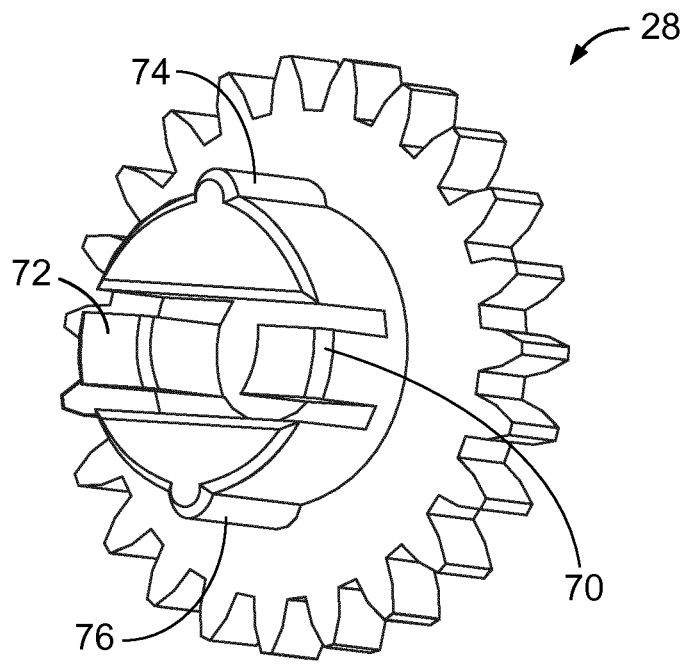
FIG. 11B illustrates a proximal perspective view of the driving gear for use with the gear assembly illustrated in FIG. 10.

The driving gear 28 is operatively coupled to the gear disc 26. FIG. 11a illustrates a front perspective view of the driving gear and FIG. 11b illustrates a back perspective view of the driving gear. As illustrated, the driving gear 28 comprises a first driving gear clip 70 and a second driving gear clip 72. It is these driving gear clips 70, 72 that engage the gear disc 26, which cannot be pressed back inward when the shaft of the motor 22 is inserted in the driving gear 28, keeping the gear disc 26 and driving gear 28 together. The driving gear 28 also comprises a first driving gear extrusion 74 and a second driving gear extrusion 76. These two gear extrusions 74, 76 are provided so as to lock into the gear disc 26 causing it to rotate along with the driving gear 28 (and the motor 22).

The transfer gear 30 resides between the driving gear and the driven gear 32. Preferably, the driven gear 32 comprises a simple spur (straight-cut) gear manufactured to a desired gearing ratio. Principally, the gear ratio determines how many turns are provided per one turn of the motor. This gearing allows the drug delivery device to control how much the plunger is going to be pushed forward. All of this is calculated by number of ramps on the gear disk 26, the gear ratio between 28 and 32 and the pitch angle on the threaded interior on the driven gear 32.

Figure 12:
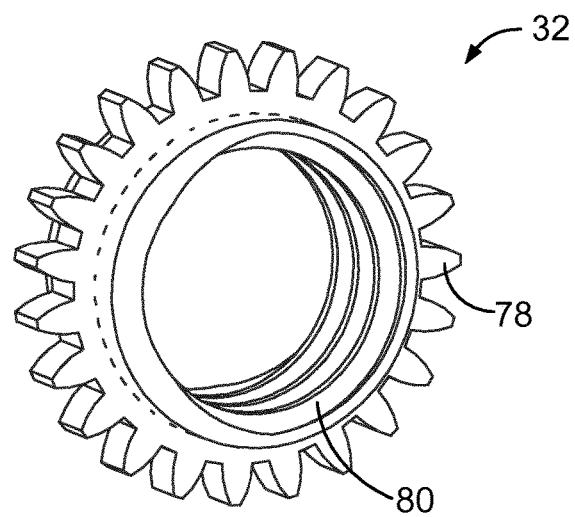
FIG. 12 illustrates a perspective view of the driven gear for use with the gear assembly illustrated in FIG. 10.
Figure 13:
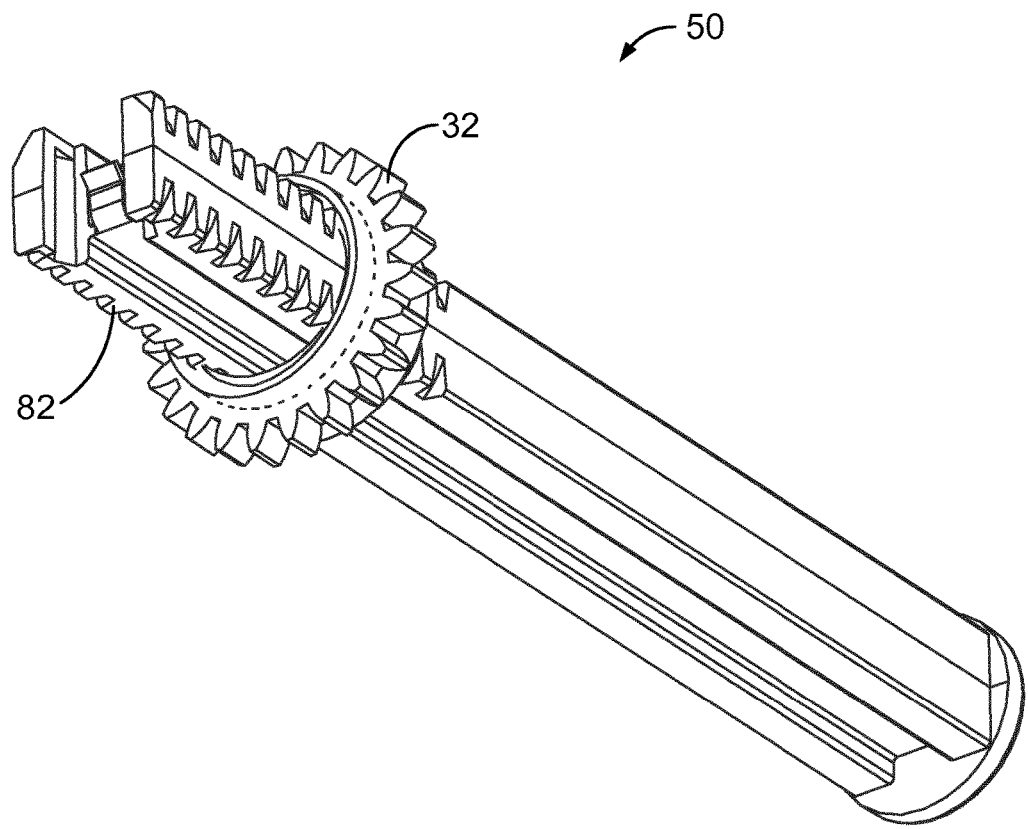
FIG. 13 illustrates a perspective view of the plunger engaged with the driven gear illustrated in FIG. 12.

FIG. 12 illustrates the driven gear 32, which comprises a spur gear exterior 78 with a spur gear threaded interior 80. The spur gear threaded interior 80 of the driven gear 32 threadedly engages piston plunger grooves 82 provided along an outer surface of the piston plunger 50. For example, FIG. 13 illustrates a perspective view of the driven gear 32 in a threaded engagement with the piston plunger groves 82 of the piston plunger 50. When the gear train 15 is activated to begin dose delivery and the driven gear 32 rotates, this rotation drives the piston plunger 50 in the distal direction, towards the plunger contained within the medicament container 54. The gear train 15 and the pitch of the thread in the spur gear threaded interior 80 and the grooves provided along the exterior of the piston plunger 50 are designed and configured so as to guarantee at least one dose per activation of gear train 15. As those of ordinary skill in the art will recognize, alternative variations in gear train gearing ratios and the pitch of the piston plunger 50 may be varied to either increase or decrease the amount of medicament to be administered per every gear train activation.

As noted above, the drug delivery device further comprises a piston plunger system 200 that is operatively coupled to the gear train 15 as illustrated in FIGS. 6 and 10. In this illustrated arrangement, the piston plunger system 200 comprises a magazine fixture 40, a plurality of plunger extensions (i.e., a first plunger extension 42 and a second plunger extension 44), a magazine flat band spring 43, a magazine body 46, a piston plunger 50, and a stopper 52.

Figure 14A:
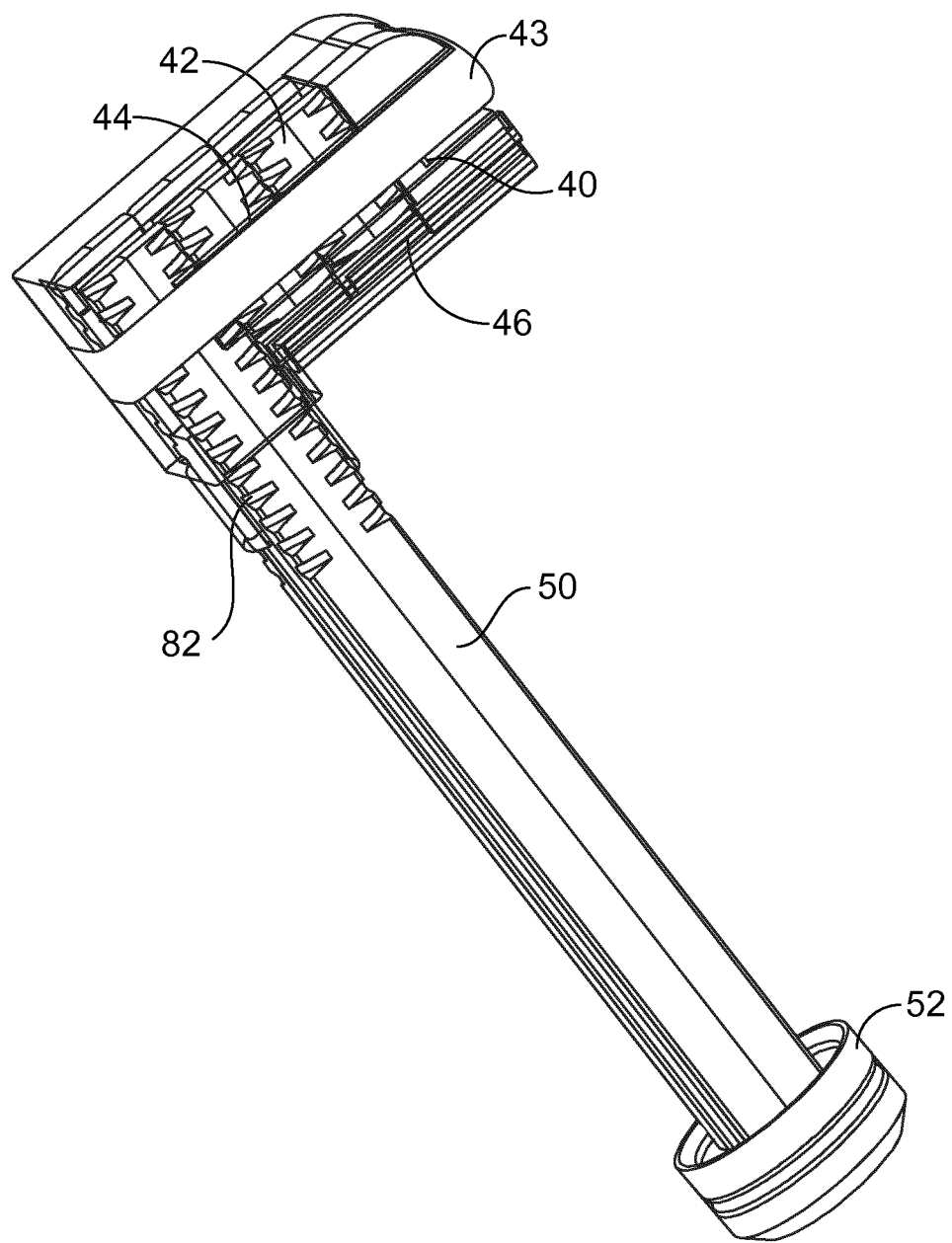
FIG. 14A illustrates a perspective view of the plunger and the plunger extensions.

The piston plunger 50 generally comprises a rectangular configuration, as shown in FIGS. 13 and 14a. As stated previously, the piston plunger 50 comprises piston plunger grooves 82 provided near a proximal end of the piston plunger so as to allow the plunger to interact with the gear threaded interior 80 of the driven gear 32. As the piston plunger 50 moves distally (towards the needle end of the device) so as to drive the stopper contained within the medicament container 54, the piston plunger is extended by clipping on the first and second plunger extensions 42 and 44 that are held in the magazine body 46.

Figure 14B:
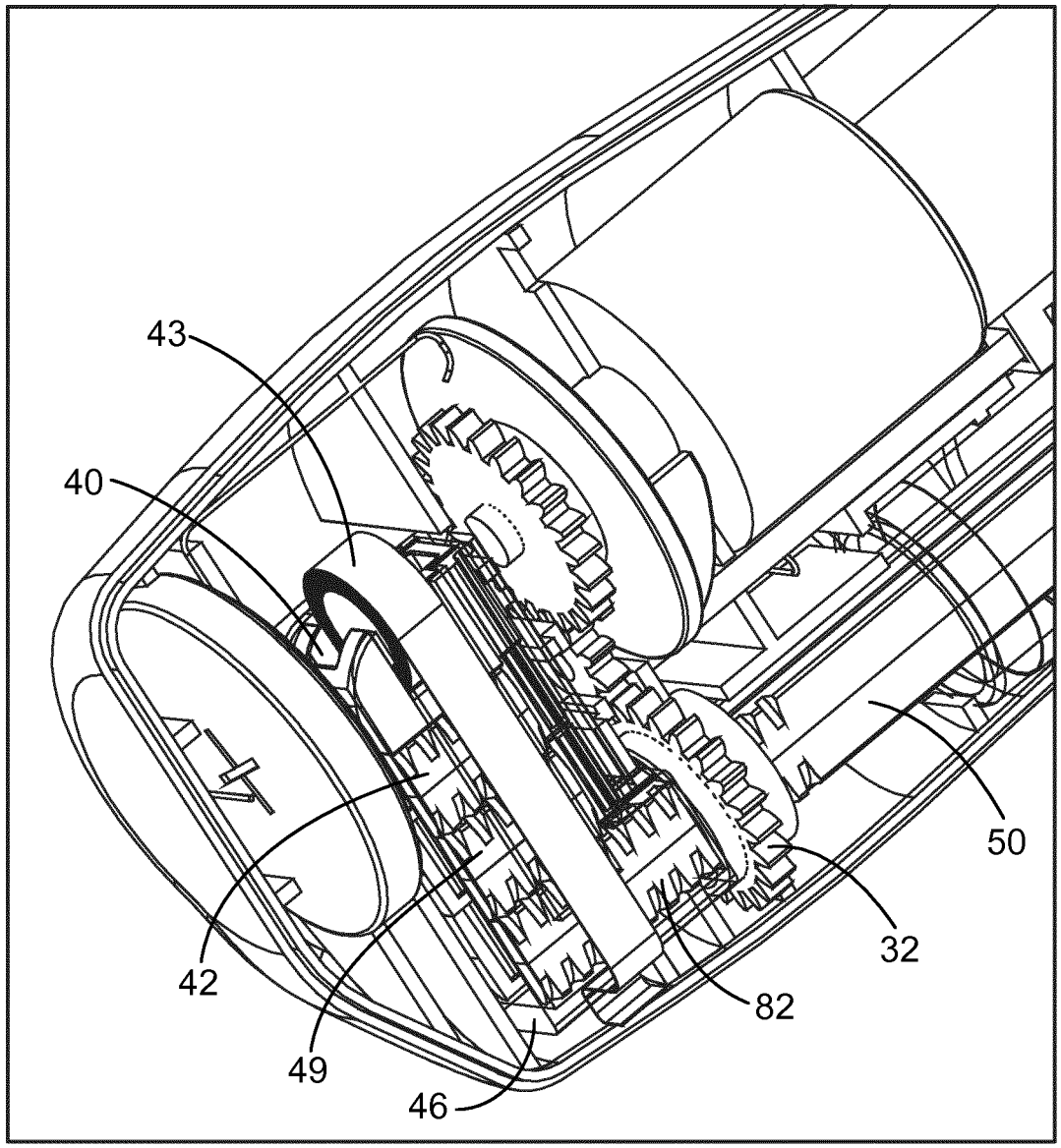
FIG. 14B illustrates a perspective view of the plunger, the plunger extensions, and the magazine flat band spring of the drug delivery device illustrated in FIGS. 1 and 2.

For example, FIG. 14b FIG. 14B illustrates a perspective view of the plunger, the plunger extensions 42, 44, and the magazine flat band spring 43 of the drug delivery device illustrated in FIGS. 1 and 2. As illustrated, the first plunger extension 42 and the second plunger extension 44 reside over one another, in a stacked arrangement within the magazine body 46 providing side supports on three sides. The pre-tensioned magazine flat band spring 43 is seated in a coiled orientation within the magazine fixture 40. As such, the magazine flat band spring 43 is also arranged having a first upper end attached to a fixture post on the magazine fixture 40. The second lower end of the magazine flat band spring 43 is attached to a bottom portion of the magazine body 46. In such an orientation, the magazine flat band spring 43 exerts a biased forced onto the top surface of the second plunger extension 44 and maintains an urging force upon this top surface of the second plunger extension 44. As such, the magazine spring forces the first and second plunger extensions 42 and 44 forward to connect to the piston plunger 50. The piston plunger 50 connects to the stopper 52 in the medicament container 54.

Figure 15A:
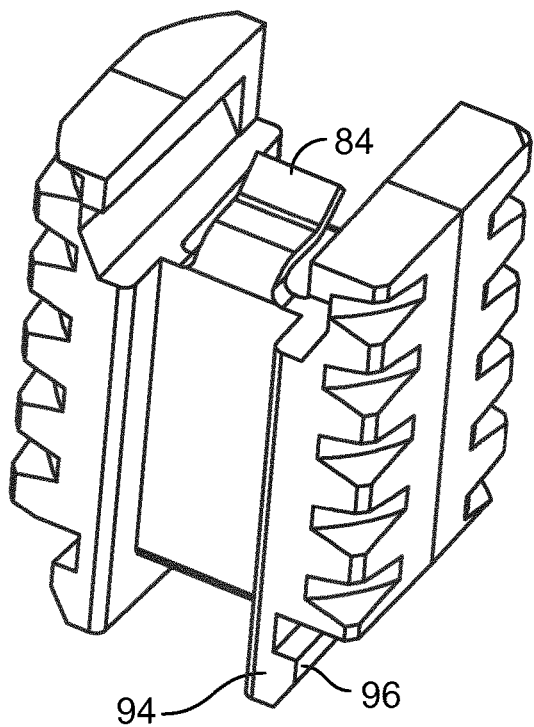
FIG. 15A illustrates a top perspective view of a plunger extension.
Figure 15B:
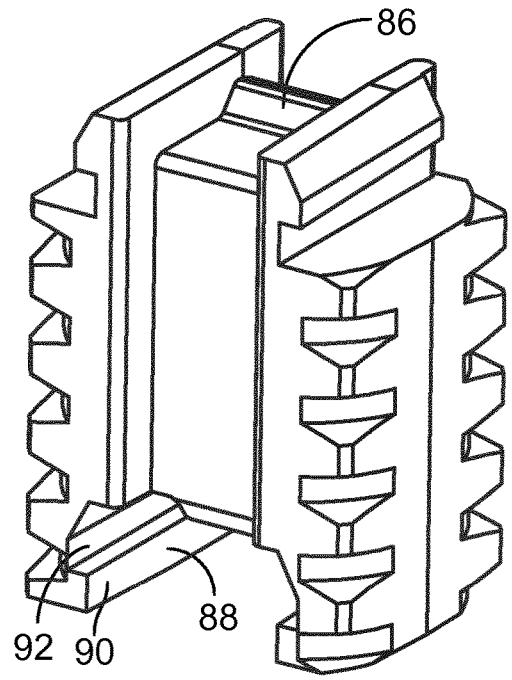
FIG. 15B illustrates a bottom perspective view of a plunger extension.

FIG. 15a illustrates a top perspective view of a plunger extension, such as the plunger extensions 42, 44. FIG. 15b illustrates a bottom perspective view of the plunger extension illustrated in FIG. 15a. Referring now to FIGS. 15a and 15b, the piston plunger 50 and first and second plunger extensions 42 and 44 have a top plunger clip mechanism 84 located on a top portion of the plunger extension. Similarly, the first and second plunger extensions 42 and 44 comprise a corresponding bottom plunger clip mechanism 86 on a bottom portion of the extensions. These clip mechanisms are configured to lock a first end of the extension to a corresponding second end of the extension together.

In addition, the top portion of each of the piston plunger 50 and first and second plunger extensions 42 and 44 further comprise vertically arranged cut-outs 88 along with the top plunger clip mechanism 84. The side walls 90 of the cut-outs 86 are arranged with generally vertically directed grooves 92, having a certain configuration. The sides of the bottom of the first and second plunger extensions 42 and 44 are arranged with a nose 94 that is designed to fit into the cut-outs 88 of an adjacent plunger extension so as to elongate the overall length of the piston plunger 50. Further, the nose 94 is arranged with generally vertically extending ledges 96. These extending ledges 96 comprises similar male configuration as the female configuration of the grooves 92 along the sidewalls 90 of the cut-outs 88. As such, where a longer piston plunger is called for during a dose administration step, the magazine spring 40 will urge a plunger extension down to reside adjacent the proximal end of the piston plunger such that the ledges 96 of the nose 94 of the subsequent extension engage into the grooves 90 of the sidewall of the already positioned extension. As such, subsequently added plunger extensions will be firmly held in place by the bottom clip mechanism 88 as it bends over the raised lip of the top plunger clip mechanism 84 and then snaps down into place behind the bottom clip 84.

During dose administration, and referring to FIG. 14b, the rotation of the spring housing 44 will cause its ratchet 52 to move around the circumference, thereby acting on the cogwheel 54 of the drive member. The rotation of the second cogwheel 62 of the drive member 54 will, due to the engagement with the drive nut 66, cause the latter to rotate. In turn, the rotation of the drive nut 66 will cause the piston plunger 50 to move in the distal direction (towards the needle end of the drug delivery device) by the engagement between the drive nut 32 and the thread segments 74 on the piston plunger. When the piston plunger 50 has moved a distance in the distal direction, a space behind the piston plunger 50 is so large that a subsequent piston plunger segment 44 may be pushed in the down vertical direction by the flat band spring 43. When the following piston plunger segments are pushed downwards in the vertical direction, they are connected to a previous piston plunger segment in that the ledges of the nose of the subsequent segment fit into the grooves of the cut-out of the previous segment, as previously described and illustrated in FIG. 15 and b. As such, the various plunger segments will sequentially "build" a continuous piston plunger 50 with one or more plunger extensions.

The piston plunger 50 may comprise a number of distinct segments being inter-connectable to each other for forming an elongated piston plunger, as described in WO 2013/153041, which is hereby incorporated entirely by reference. In this illustrated arrangement, the piston plunger segments are arranged in a stack and are interconnected successively during delivery of a dose of medicament.

Figure 16:
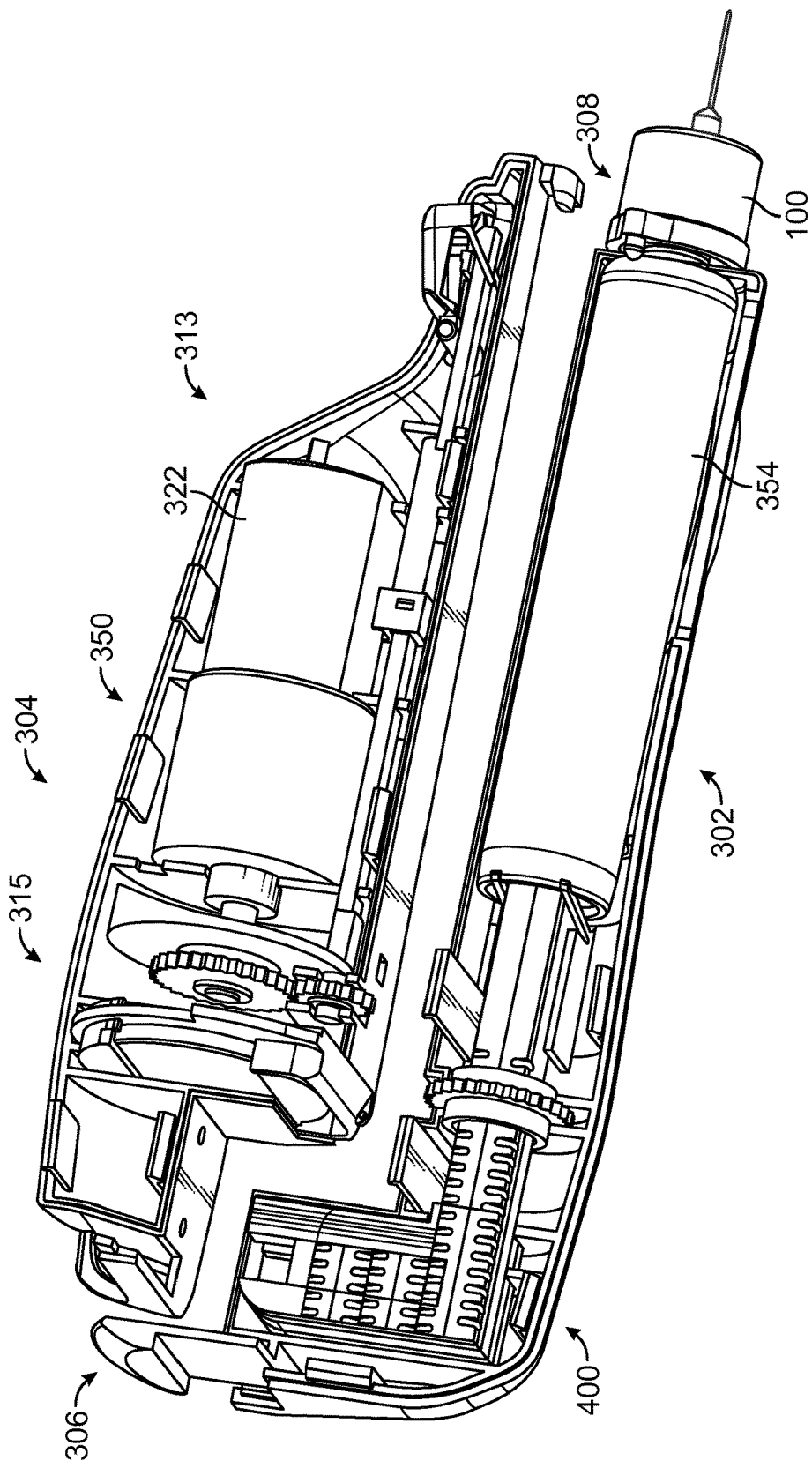
FIG. 16 illustrates a plan view of a semi-disposable motorized injection device in accordance with one aspect of the present disclosure, with one housing part removed for clarity.

As previously discussed, in an alternative arrangement, the injection device 10 comprises a reusable injection device. With such a reusable injection device, once the medicament contained within the medicament container 54 is depleted, the medicament container 54 may be removed and replaced with a new medicament container. For example, FIG. 16 illustrates one arrangement of a semi-disposable injection device 310. As illustrated, this injection device 310 comprises a disposable portion 302 and a re-usable portion 304. In this arrangement, the disposable portion 302 may utilize various clipping features 306, 308 to removably connect itself onto the reusable portion 304. As illustrated, the reusable portion 304 comprises an activation system 313, a motor 322, a gear train 315, and an injection circuit 350, all as previously described herein.

In this arrangement, the disposable portion 302 comprises a multiple segmented piston plunger system 400 coupled to a medicament container 354, all as previously described herein.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A motorized drug delivery device configured to administer at least one pre-set dose of a medicament contained within a medicament container, the delivery device comprising:
   a user activation system;
   a motor;
   a gear train operatively coupled to the user activation system and the motor;
   a piston plunger system operatively coupled to the gear train, the piston plunger system comprising a piston plunger and at least one plunger extension for extending a length of the piston plunger;
   wherein the piston plunger system is configured to act on a stopper contained within the medicament container to deliver at least one pre-set dose of medicament,
   wherein the user activation system comprises a mechanical automatic reset activation system that automatically resets the drug delivery device after administration of the pre-set dose, and wherein the mechanical automatic reset activation system includes a dispense button operatively coupled to a hook release.

2. The drug delivery device of claim 1, wherein the activation system further comprises a spring disposed about a proximal end of the hook release.

3. The drug delivery device of claim 2, further comprising a connection rod engaged with the proximal end of the hook release.

4. The drug delivery device of claim 3, wherein the gear train comprises
   a gear disc, a driving gear, a transfer gear, and a driven gear.

5. The drug delivery device of claim 4 wherein the gear disc is operatively coupled to an output shaft of the motor.

6. The drug delivery device of claim 5, wherein the gear disc comprises a first inclined wall.

7. The drug delivery device of claim 6, wherein the first inclined wall of the gear disc is operatively coupled to the connection rod during dose administration.

8. The drug delivery device of claim 7, wherein when the first inclined wall of the gear disc is operatively coupled to the connection rod, an injection circuit is completed so as to initiate dose administration.

9. The drug delivery device of claim 4, wherein
   the transfer gear is operatively coupled between the driving gear and the driven gear.

10. The drug delivery device of claim 4, wherein
    the driven gear comprises a threaded interior.

11. The drug delivery device of claim 10, wherein the threaded interior engages a groove provided on an outer surface of the piston plunger.

12. The drug delivery device of claim 4,
    wherein rotation of the driven gear drives the piston plunger.

13. The drug delivery device of claim 12, wherein rotation of the driven gear drives the piston plunger in a distal direction during dose administration.

14. The drug delivery device of claim 1, wherein the piston plunger system comprising the piston plunger and at least one plunger extension for extending the length of the piston plunger comprises:
    a first plunger extension and a second plunger extension.

15. The drug delivery device of claim 14, wherein the first and second plunger extensions are configured to be inter-connectable to each other for forming an elongated piston plunger.

16. The drug delivery device of claim 15, wherein the first and second plunger extensions are interconnected during dose administration.

17. The drug delivery device of claim 15, wherein the piston plunger system further comprises a magazine stack,
    wherein the first and second plunger extensions are arranged in the magazine stack.

18. The drug delivery device of claim 17, further comprising
    a magazine spring for exerting a biased force onto one of the first or second plunger extensions so as to maintain an urging force upon the first and second plunger extensions.

19. The drug delivery device of claim 18, wherein the magazine spring comprises a flat band spring.

\* \* \* \* \*